United States Patent [19]

Harnden et al.

[11] Patent Number: 5,252,575
[45] Date of Patent: Oct. 12, 1993

[54] ANTIVIRAL PURINE DERIVATIVES WITH IMPROVED GASTROINTESTINAL ABSORPTION

[75] Inventors: Michael R. Harnden, Epsom; Paul G. Wyatt, Surrey; Leslie J. A. Jennings, Epsom, all of England

[73] Assignee: Beecham Group p.l.c., Brentford, England

[21] Appl. No.: 886,710

[22] Filed: May 21, 1992

Related U.S. Application Data

[63] Continuation-in-part of Ser. No. 564,731, Aug. 8, 1990, abandoned.

[51] Int. Cl.⁵ .................... A61K 31/52; C07D 473/18; C07D 473/26
[52] U.S. Cl. .................... 514/261; 514/262; 544/276; 544/277; 544/323; 564/301
[58] Field of Search .............. 544/276, 277; 514/261, 514/262

[56] References Cited

FOREIGN PATENT DOCUMENTS 0242482 10/1987 European Pat. Off. .
0294069 12/1988 European Pat. Off. .
0298601  1/1989 European Pat. Off. .
0313289  4/1989 European Pat. Off. .

OTHER PUBLICATIONS

*Chemical Abstracts,* vol. 109, No. 15, abs. No. 129567p, from Harnden et al., *Tetrahedron Lett.* 1988, 29(6), 701–4.

*Primary Examiner*—Mark L. Berch
*Attorney, Agent, or Firm*—Hopgood, Calimafde, Kalil, Blaustein & Judlow

[57] ABSTRACT

Compounds of formula (I) and pharmaceutically acceptable salts thereof:

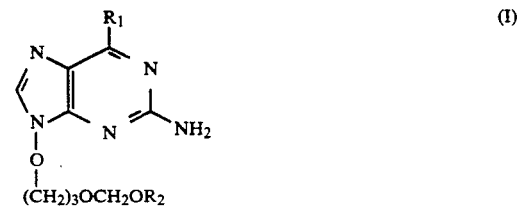

(I)

wherein
$R_1$ is hydrogen or hydroxy; and
$R_2$ is $C_{1-6}$ alkyl;

which are pro-drugs for 9-(3-hydroxyprop-1-oxy)guanine having antiviral activity, a process for their preparation and their use as pharmaceuticals.

7 Claims, 2 Drawing Sheets

FIGURE 1

FIGURE 2

ANTIVIRAL PURINE DERIVATIVES WITH IMPROVED GASTROINTESTINAL ABSORPTION

This is a continuation-in-part application of application U.S. Ser. No. 564,731, filed Aug. 8, 1990, abandoned.

The present invention relates to novel compounds which are of potential use as antiviral agents, to a process for their preparation and to their use as pharmaceuticals.

EP-A-242482 (Beecham Group p.l.c.), the subject matter of which is incorporated herein by reference, discloses antiviral compounds of formula (A) and pharmaceutically acceptable salts thereof:

(A)

wherein
- $R_a$ is hydrogen or $CH_2OH$;
- $R_b$ is hydrogen or, (when $R_a$ is hydrogen), hydroxy or $CH_2OH$;
- $R_c$ is $CH_2OH$ or, (when $R_a$ and $R_b$ are both hydrogen), $CH(OH)CH_2OH$;
- $R_d$ is hydrogen, hydroxy, amino or $OR_e$ wherein
- $R_e$ is $C_{1-6}$ alkyl, phenyl or phenyl $C_{1-2}$ alkyl either of which phenyl moieties may be substituted by one or two halo, $C_{1-4}$ alkyl or $C_{1-4}$ alkoxy groups;

and in which any OH groups in $R_a$, $R_b$ and/or $R_c$ may be in the form of O-acyl, phosphate, cyclic acetal or cyclic carbonate derivatives thereof.

Compounds wherein $R_d$ is other than hydroxy are pro-drugs for the compounds of formula (A) wherein $R_d$ is hydroxy. Example 1 describes the compound of formula (I) wherein $R_a$ and $R_b$ are both hydrogen, $R_c$ is $CH_2OH$ and $R_d$ is hydroxy which is 9-(3-hydroxyprop-1-oxy)guanine, hereinafter referred to as E1 or BRL 44385.

It has now been discovered that certain derivatives of E1 are pro-drugs for E1, having improved gastrointestinal absorption properties.

Accordingly, the present invention provides a compound of formula (I) or a pharmaceutically acceptable salt thereof:

(I)

wherein
- $R_1$ is hydrogen or hydroxy; and
- $R_2$ is $C_{1-6}$ alkyl.

Suitable values for $R_2$ alkyl groups include methyl, ethyl, n- and iso-propyl, n-, iso-, sec- and tert-butyl and pentyl (all possible isomers), particularly iso-propyl.

Pharmaceutically acceptable salts are as described in EP-A-242482.

The compounds of formula (I) including their alkali metal salts may form solvates such as hydrates and these are included wherever a compound of formula (I) or a salt thereof is herein referred to.

It will be appreciated that, when $R_1$ is hydroxy in formula (I) the compound exists in the predominant tautomeric form of structure (IA):

(IA)

The invention also provides a process for the preparation of a compound of formula (I), or a pharmaceutically acceptable salt thereof, which process comprises either i) imidazole ring closure of a compound of formula (II):

(II)

wherein Q is a group capable of cyclising to form an imidazole ring, such as amino or an amino derivative, for example, formylamino; or ii) pyrimidine ring closure of a compound of formula (III):

(III)

wherein Y is amino or $C_{1-6}$ alkoxy, with a condensing agent capable of cyclising to form a pyrimidine ring having a 2-$NHR_x$ substituent, resulting in a compound of formula (I) wherein $R_1$ is hydroxy; or iii) condensing a compound of formula (IV):

(IV)

with a side chain intermediate of formula (V):

$$R_5O(CH_2)_3Z \quad (V)$$

wherein Z is a leaving group;

and wherein, in formulae (II) to (V), $R_5$ is $CH_2OR_2$ or a group or atom convertible thereto, $R_1'$ is $R_1$ or a group or atom convertible thereto, $R_x$ is hydrogen or an amino protecting group; and thereafter, when desired or necessary, converting $R_5$ and/or $R_1'$, when other than $CH_2OR_2$ and/or $R_1$, to $CH_2OR_2$ and/or $R_1$ respectively, and/or converting $R_5$ and/or $R_1'$ when $CH_2OR_2$ and/or $R_1$ to other $CH_2OR_2$ and/or $R_1$ and/or converting $R_x$ when an amino protecting group, to hydrogen.

Process i) may be carried out, preferably when Q is formylamino, using a cyclisation condensing agent, such as diethoxymethyl acetate or triethyl orthoformate, or by fusion.

Process ii) is preferably carried out in accordance with the methods described in EP-A-242482, the subject matter of which is incorporated herein by reference.

Process iii) may be carried out with suitable values for Z including hydroxy and halo, such as chloro, bromo and iodo, preferably iodo; or other groups readily displaceable by nucleophiles, such as mesyloxy or tosyloxy. The reaction preferably takes place in an inert solvent, such as dimethylformamide at 0°-50° C., preferably ambient temperature. When Z is hydroxy, the reaction takes place in the presence of a dehydrating agent, such as diethyl azodicarboxylate in the presence of triphenylphosphine. When Z is halo, the reaction preferably takes place in the presence of a base, such as potassium carbonate.

Examples of conversions of variable groups are as follows:

$R_1'—R_1$ a) An $R_1$ hydroxy group may be converted to $R_1'$ is chloro, by chlorination using a reagent such as phosphorus oxychloride, preferably in the presence of tetraethylammonium chloride and dimethylaniline (as acid acceptor) in $CH_3CN$ at reflux temperatures, according to the method described by M. J. Robins and B. Ozanski, Can. J. Chem, 59, 2601 (1981).

b) When $R_5$ is other than $CH_2OR_2$, an $R_1'$ chloro group may be converted to $R_1$ is hydroxy by hydrolysis using aqueous mineral acid, such as hydrochloric acid, or more preferably, using an organic acid, such as formic acid at elevated temperature, suitably 70°-150° C., preferably around 100° C.

c) An $R_1'$ chloro group may be converted to $R_1'$ is methoxy by reaction with sodium methoxide. The $R_1'$ is methoxy group may in turn be converted to $R_1'$ is hydroxy by hydrolysis using non-acidic methods, preferably using mercaptoethanol.

d) An $R_1'$ alkoxy group, such as methoxy, may also be converted to $R_1$ hydroxy by the methods of D. R. Haines, J. Med. Chem. 1987, 30, 943 and K. K. Ogilvie and H. R. Hanna, Can. J. Chem. 1984, 62, 2702.

$R_5—CH_2OR_2$ a) $R_5$ hydrogen may be converted to $CH_2OR_2$ by conventional procedures for preparing acetals, using $LCH_2OR_2$ wherein L is a leaving group, such as chloro or acetate.

b) $R_5$ hydrogen may be replaced by a protecting group, which may be removed by conventional deprotection methods, and then subsequently converted to $CH_2OR_2$ as in a) above.

Suitable examples of protecting groups and processes for their removal, are as described in EP-A-242482.

Particularly suitable protecting groups include the benzyl group, removed by catalytic hydrogenation; the acetate group removed by acid hydrolysis, 2M HCl in ethanol; or the t-butyldimethylsilyl group removable by 80% acetic acid at elevated temperature, around 90° C.

$R_x'—R_x$ $R_x'$ may be formyl, which may be converted to $R_x$ is hydrogen by hydrolysis, preferably under basic conditions.

It will be appreciated that the above conversions may take place in any desired or necessary order, having regard to the final desired compound of formula (I), and that interconversions involving acid conditions could affect the $OCH_2OR_2$ moiety in formula (I).

It is normally preferred that $R_5$ in the aforedescribed processes is $CH_2OR_2$ as defined.

Intermediates of formula (II) may be prepared from a corresponding compound of formula (VI):

(VI)

and via intermediates of formula (V) wherein Z is OH, as hereinbefore defined, according to the methods described in EP-A-242482 i.e. by converting the compound of formula (V) wherein Z is OH to the phthalimidooxy derivative followed by reaction with methylhydrazine, as described in the Descriptions hereinafter.

The compound of formula (VI) wherein $R_1'$ is chloro and $R_x$ is hydrogen, is a known compound as described by Temple et. al., J. Org. Chem., 40 (21), 3141, 1975.

Intermediates of formula (III) may be prepared according to the methods described in EP-A-242482.

Compounds of the formula (IV) are prepared as described in EP-A-313289 (Beecham Group p.l.c.) from compounds of formula (VI) wherein the 5-amino group is formylated, by reaction with $R_6ONH_2$ wherein $R_6$ is a protecting group, to give a compound of formula (VII):

(VII)

which may be cyclised with diethoxymethyl acetate, to give a compound of formula (IV) wherein the OH group is protected. Suitable values for $R_6$ include benzyl, removable by hydrogenation, and the tetrahydropyran-2-yl group removable by treatment with 80% acetic acid, at ambient temperature.

Intermediates of the formula (V) wherein Z is hydroxy are known compounds or are prepared by analogous methods to those used for structurally similar known compounds.

Intermediates of formulae (II), (III) and (V) but wherein Z is replaced by an aminooxy group, and wherein $R_5$ is $CH_2OR_2$, are believed to be novel and form an aspect of the invention.

Pharmaceutically acceptable salts may be prepared in conventional manner, for example, in the case of acid addition salts, by reaction with the appropriate organic or inorganic acid.

The compounds of the invention are potential use in the treatment of infections caused by viruses, especially herpesviruses such as herpes simplex type 1, herpes simplex type 2, varicella-zoster and Epstein-Barr virus.

Compounds of the invention may be formulated for use in a pharmaceutical composition. Accordingly, in a further aspect of the invention, there is provided a pharmaceutical composition which comprises a compound of formula (I) or pharmaceutically acceptable salt thereof together with a pharmaceutically acceptable carrier or excipient.

A composition which may be administered by the oral route to humans may be compounded in the form of a syrup, tablet or capsule. When the composition is in the form of a tablet, any pharmaceutical carrier suitable for formulating such solid compositions may be used, for example magnesium stearate, starch, lactose, glucose, rice, flour and chalk. The composition may also be in the form of an ingestible capsule, for example of gelatin, to contain the compound, or in the form of a syrup, a solution or a suspension. Suitable liquid pharmaceutical carriers include ethyl alcohol, glycerine, saline and water to which flavouring or colouring agents may be added to form syrups. The compounds may also be presented with a sterile liquid carrier for injection.

The composition may also be formulated for topical application to the skin or eyes.

For topical application to the skin, the composition may be in the form of a cream, lotion or ointment. These formulations may be conventional formulations well known in the art, for example, as described in standard books of pharmaceutics and cosmetics, such as Harry's Cosmeticology published by Lenoard Hill Books and the British Pharmacopaeia.

The composition for application to the eyes may be a conventional eye-drop composition well known in the art, or an ointment composition.

Preferably, the composition of this invention is in unit dosage form or in some other form that may be administered in a single dose. A suitable dosage unit might contain from 50 mg to 1 g of active ingredient, for example 100 to 500 mg.

Such doses may be administered 1 to 4 times a day or more usually 2 or 3 times a day. The effective dose of compound will in general be in the range of from 1.0 to 20 mg/kg of body weight per day or more usually 2.0 to 10 mg/kg per day.

No unacceptable toxicological effects are indicated at the above described dosage levels.

The invention also provides a method of treating viral infections in a human or non-human animal, which comprises administering to the animal an effective, nontoxic amount of a compound of formula (I) or a pharmaceutically acceptable salt thereof.

The invention also provides a compound of formula (I) or a pharmaceutically acceptable salt thereof for use as an active therapeutic substance, in particular for the treatment of viral infections.

The compounds of the invention are also believed to exhibit a synergistic antiviral effect in conjunction with interferons; and combination products comprising these two components for sequential or concomitant administration, by the same or different routes, are therefore within the ambit of the present invention.

The following examples illustrate the invention; the following descriptions illustrate the preparation of intermediates.

DESCRIPTION 1

Intermediates for Example 1 a) 3-(Isopropoxymethoxy)propanol

A solution of 1,3-propanediol (19.4 g, 255 mmol) in dry tetrahydrofuran (100 ml) under nitrogen at 0°–5° C. was treated with sodium hydride (2.04 g, 85 mmol) and stirred for 1 hour. Chloromethylisopropyl ether (9 g, 83 mmol) in dry tetrahydrofuran (15 ml) was added over 15 min. Stirring was continued for a further 2 hours. The reaction mixture was filtered and the filtrate was evaporated in vacuo. The residue was purified by column chromatography on silica eluting with dichloromethane:methanol (97:4) to give the title compound as a colourless oil. (5.3 g, 44%). $\nu_{max}$ (Film) 3400, 2910, 2860, 2805, 2760, 1460, 1440, 1425, 1410 and 1380 cm$^{-1}$; $\delta_H$ (CDCl$_3$) 1.17 (3H, s, CH$_3$), 1.20 (3H, s,CH$_3$), 1.84 (2H, quintet, J=6 Hz CH$_2$CH$_2$CH$_2$), 2.3 (1H, br s, D$_2$O exchangeable OH), 3.72 (2H, t, J=6 Hz, CH$_2$OCH$_2$OCH(CH$_3$)$_2$) 3.76 (2H, t, J=6 Hz,CH$_2$ON), 3.86 (1H, m, CH(CH$_3$)$_2$), 4.70 (2H, s, OCH$_2$O).

b) N-[3-(Isopropoxymethoxy)propoxy]phthalimide

A mixture of [3-(isopropoxymethoxy)propanol (5.3 g, 35.8 mmol), N-hydroxyphthalimide (5.83 g, 35.8 mmol) and triphenylphosphine (10.48 g, 40 mmol) in dry tetrahydrofuran (75 ml) at 0°–5° C.; was treated with a solution of diethyl azodicarboxylate (6.96 g, 40 mmol) in dry tetrahydrofuran (15 ml) over 15 min. The reaction mixture was stirred at ambient temperature for 18 hr. The solvent was removed in vacuo and the residue was dissolved in diethyl ether (100 ml) and cooled to 5° C. for 2 hr. The solid was filtered off, the filtrate evaporated in vacuo, and the residue purified by column chromatography on silica eluting with hexane:ethyl acetate (70:30) to give the title compound as an oil (9.3 g, 88%). $\nu_{max}$ (Film) 2980, 2940, 2900, 1740, 1475 and 1380 cm$^{-1}$; $\delta_H$(CDCl$_3$) 1.17 (3H, s, CH$_3$), 1.19 (3H, s, CH$_3$), 2.06 (2H, quintet, J=6.3 Hz CH$_2$CH$_2$CH$_2$), 3.77 (2H, t, J=6.3 Hz, CH$_2$OCH$_2$OCH(CH$_3$)$_2$), 3.88 (1H, septet, J=6.3 Hz, OCH(CH$_3$)$_2$), 4.32 (2H, t, J=6.3 Hz CH$_2$ON), 4.73 (2H, s, OCH$_2$O), 7.78 (4H, m, ArH). (Found: C, 16.53; H, 6.59; N, 4.71%: C$_{15}$H$_{19}$NO$_5$ requires: C, 16.42; H, 6.52; N, 4.77%).

c) N-[3-(Isopropoxymethoxy)propoxyamine

A solution of N-[3-(isoproxymethoxy)propoxy]phthalimide (9.3 g, 31.7 mmol) in dry dichloromethane (70 ml) at ambient temperature was treated with N-methylhydrazine (2.2 g, 47.8 mmol) and stirred for 2 hours. The reaction mixture was filtered, the filtrate evaporated in vacuo and the residue purified by column chromatography on silica eluting with hexane: ethyl acetate (60:40) to give the title compound as a colourless oil (4.2 g, 82%). $\nu_{max}$ (Film) 3310, 3220, 3160, 2960, 2920, 2870, 1580, 1465 and 1380 cm$-^1$; $\delta_H$ (CDCl$_3$) 1.10 (3H, s, CH$_3$), 1.18 (3H, s, CH$_3$), 1.80 (2H, quintet, J=6.3 Hz CH$_2$CH$_2$CH$_2$), 3.52 (2H, t, J=6.3 Hz, CH$_2$OCH- $_2$OCH(CH$_3$)$_2$), 3.66 (2H, t, J=6.3 Hz CH$_2$ON), 3.8 (1H, septet, J=6.3 Hz OCH(CH$_3$)$_2$), 4.65, (2H, s, OCH$_2$O), 5.2-55 (2H, br s, D$_2$O exchangeable NH$_2$).

d)
4-Chloro-2,5-diformamido-6-[(3-isopropoxymethoxy)-propoxy]aminopyrimidine A mixture of 4,6-dichloro-2,5-diformamidopyrimidine (2.9 g, 12.3 mmol), 3-(isopropoxymethoxy)propoxyamine (2.0 g, 12.2 mmol) and N,N-diisopropylethylamine (4.3 ml, 3.19 g, 24.6 mmol) in diglyme (50 ml) was heated to 100° for 3 hr. The cooled reaction mixture was filtered, and the filtrate was evaporated in vacuo. The residue was purified by column chromatography on silica eluting with ethyl acetate:hexane (1:1) then ethyl acetate to give the title compound as a yellow gum, which crystallised from ethyl acetate (3.0 g, 75%) mp 132.4° C. $\nu_{max}$(KBr) 3250, 2960, 2910, 2870, 1705, 1645, 1590, 1565, 1495, 1460 and 1380 cm$^{-1}$; δH [(CD$_3$)$_2$SO], 1.08 (3H, s, CH$_3$), 1.10 (3H, s, CH$_3$), 1.84 (2H, quintet, J=6.3 Hz, CH$_2$; CH$_2$CH$_2$), 3.58 (2H, t, J 6.3 Hz, CH$_2$OCH$_2$OCH(CH$_3$)$_2$), 3.76 (1H, septet, J=6.3 Hz, OCH(CH$_3$)$_2$), 3.93 (2H, t, J 6.3 Hz, CH$_2$ON), 4.61 (2H, s, OCH$_2$O), 8.14 (1H, s, NHCHO), 9.25 (1H, br.s, NHCHO), 9.39 (1H, br. s, D$_2$O exchangeable NHOCH$_2$), 10.6-11.0 (2H, br, D$_2$O exchangeable, 2×NHCHO). (Found: C, 43.20; H, 5.55; N, 19.24%. C$_{13}$H$_{20}$N$_5$O$_5$Cl requires: C, 43.15; H, 5.57; N, 19.35%).

DESCRIPTION 2

Intermediates for Example 2 a) 3-(Methoxymethoxy)propanol

A solution of 1,3-propanediol (25.1 g, 330 mmol) in dry tetrahydrofuran (10 ml) was treated with sodium hydride (80%, 3.3 g, 110 mmol) at room temperature under nitrogen. The solution was stirred at ambient temperature for 30 min. then chloromethylmethyl ether (8.85 g, 110 mmol) was added dropwise with stirring in dry tetrahydrofuran (15 ml), maintaining the temperature at 10° C. (ice bath). The reaction was stirred for 2 hr. then filtered and the filtrate was evaporated in vacuo. The residue was purified by column chromatography on silica eluting with dichloromethane:methanol (97:3) to give the title compound as a colourless oil (7.0 g, 53%). $\nu_{max}$(Film) 3400, 2920, 2880, 2760, 1460, 1435, and 1380 cm$^{-1}$; δ$_H$(CDCl$_3$) 1.8 (2H, quintet, J=6 Hz, CH$_2$CH$_2$CH$_2$), 3.1 (1H, s, D$_2$O exchangeable, OH), 3.35 (3H, s, OCH$_3$), 3.7 (4H, m, CH$_2$OH, CH$_2$OCH$_2$OCH$_3$), 4.65 (2H, s, OCH$_2$O).

N-[3-(Methoxymethoxy)propoxy]phthalimide

A solution of 3-(methoxymethoxy)propanol (5 g, 41.6 mmol), triphenylphosphine (13.1 g, 50 mmol) and N-hydroxyphthalimide (7.25 g, 44 mmol) in dry tetrahydrofuran (150 ml) was cooled to 0°-5° C. and treated with diethyl azodicarboxylate (8.7 g, 50 mmol) in dry tetrahydrofuran (10 ml) over ½ hr. The reaction was then stirred at ambient temperature for 18 hr. The solvent was removed in vacuo and the residue was dissolved in diethyl ether (100 ml) and the mixture cooled to 0°-5° C. for 3 hr. The solid was removed by filtration and the filtrate was evaporated in vacuo. The residue was purified by column chromatography on silica eluting with hexane:ethyl acetate (70:30) to give the title compound as an oil (4.5 g, 41%). $\nu_{max}$(Film) 2960, 2900, 1800, 1740, 1620, 1480 and 1380 cm$^{-1}$; δ$_H$(CDCl$_3$) 2.07 (2H, quintet, J=6.3 Hz, CH$_2$CH$_2$CH$_2$), 3.38 (3H, s, OCH$_3$), 3.77 (2H, t, J=6.3 Hz, CH$_2$OCH$_2$OCH$_3$), 4.33 (2H, t, J=6.3 Hz, CH$_2$ON), 4.66 (2H, s, OCH$_2$O), 7.83 (4H, m, ArH).

c) 3-Methoxymethoxypropoxyamine

A solution of N[3-(methoxymethoxy)propoxy]phthalimide (4.5 g, 17 mmol) in dry dichloromethane (50 ml) was cooled to 0°-5° and treated with N-methylhydrazine (1.2 g, 26 mmol). The reaction mixture was stirred for 2 hr then filtered and the filtrate was evaporated in vacuo. The residue was purified by column chromatography on silica eluting with hexane:ethyl acetate (60:40) to give the title compound as a colourless oil (1.1 g, 50%). $\nu_{max}$(Film) 3310, 3240, 3160, 2960, 2910, 1590, 1465, and 1380 cm$^{-1}$; δ$_H$(CDCl$_3$) 2.07 (2H, quintet, J=6.3 Hz, CH$_2$CH$_2$CH$_2$), 3.38 (3H, s, CH$_3$O), 3.50 (2H, t, J=6.3 Hz, CH$_2$OCH$_2$OCH$_3$), 3.70 (2H, t, J 6.3 Hz, CH$_2$ONH$_2$), 4.66 (2H, s, OCH$_2$O), 5.2-5.5 (2H, br.s, D$_2$O exchangeable, NH$_2$).

d)
4-Chloro-6-[3-(methoxymethoxy)propoxy]amino-2,5-diformamidopyrimidine A mixture of 4,6-dichloro-2,5-diformamidopyrimidine (1.75 g, 7.4 mmol), 3-(methoxymethoxy)propoxyamine (1.0 g, 7.4 mmol) and N,N-diisopropylethylamine (2 g, 15.5 mmol) in dry diglyme was heated to 100° C. for 2 hr. The cooled reaction mixture was filtered and the filtrate was evaporated in vacuo. The residue was purified by column chromatography on silica eluting with ethyl acetate:hexane (50:50) then ethyl acetate to give the title compound as a yellow oil which was crystallised from ethyl acetate (1.2 g, 50%) mp 136°-8° C. $\nu_{max}$ (KBr) 3240, 2920, 2880, 1705, 1640, 1590, 1565, 1495, 14650, 1410, and 1380 cm$^{-1}$; δ$_H$ [(CD$_3$)$_2$SO]1.85 (2H, quintet, J=6.3 Hz, CH$_2$CH$_2$CH$_2$), 3.24 (3H, s, OCH$_3$), 3.58 (2H, t, J=6.3 Hz, CH$_2$OCH$_2$OCH$_3$), 3.94 (2H, t, J=6.3 Hz, CH$_2$ONH), 4.5 (2H, s, OCH$_2$O), 8.15 (1H, s, NHCHO), 9.26 (1H, d, J=9.6 Hz, collapses to singlet on D$_2$O, NHCHO), 9.4 (1H, s, D$_2$O exchangeable NHOCH$_2$), 10.73 (1H, s, D$_2$O, exchangeable NHCHO), 10.84 (1H, d, J=9.6 Hz, D$_2$O exchangeable, NHCHO).

DESCRIPTION 3

Intermediate for Examples 4 and 5

3-(Ethoxymethoxy)propan-1-ol

A solution of chloroethylethyl ether (50 mmol) in dry tetrahydrofuran (10 ml) was added dropwise at 0°-5° C. to a stirred solution of 1,3-propanediol (150 mmol) in dry tetrahydrofuran (100 ml) and N,N-diisopropylethylamine (75 mmol). The mixture was stirred for 2 hours at room temperature, the solvent was evaporated in vacuo and the residue was purified by column chromatography on silica, eluting with dichloromethane:methanol (98:2) to give the title compound as a colourless oil (5.6 g, 83%); $\nu_{max}$(Film) 3420, 2980, 2940, 2880, 1480, 1445, 1390 and 1180 cm$^{-1}$; δ$_H$(CDCl$_3$) 1.20 (3H, t, J=6.5 Hz, CH$_3$CH$_2$), 1.8 (2H, m, CH$_2$CH$_2$CH$_2$), 3.2 (1H, s, OH), 3.6 (6H, m, CH$_2$OH, CH$_2$O and CH$_3$CH$_2$), 4.8 (2H, s, OCH$_2$O).

EXAMPLES

The following compounds of formula (I) were prepared.

| Example No | R₁ | R₂ | |
|---|---|---|---|
| 1 | H | (CH₃)₂CH | BRL 55792 |
| 2 | H | CH₃ | BRL 55791 |
| 3 | OH | (CH₃)₂CH | BRL 57037 |
| 4 | OH | C₂H₅ | BRL 57040 |
| 5 | H | C₂H₅ | BRL 57041 |

EXAMPLE 1

2-Amino-9-[3-(isopropoxymethoxy)propoxy)purine a) A mixture of 4-chloro-2,5-diformamido-6-[3-(isopropoxymethoxy)propoxyamino]pyrimidine (3.3 g, 9.12 mmol) and diethoxymethyl acetate (10 ml) was heated at 120° C. for 1 hr. The solution was then evaporated and the residue taken up into methanol (30 ml) and concentrated aqueous ammonia (3 ml). After 1 hr. at 20° C. the solvent was removed and the residue purified by column chromatography on silica gel eluting with hexane:ethyl acetate (1:1) to afford 6-chloro-2-formamido-9-[3-(isopropoxymethoxy)propoxy]purine (1.89 g; 60%), $\nu_{max}$ (KBr) 2970, 1697, 1609, 1581, 1503, 1383 cm$^{-1}$; $\delta_H$[(CD₃)₂SO], 1.10 (6H, d, J=6.3 Hz, 2×CH₃), 1.97 (2H, quintet, J=6.3 Hz, CH₂C$\underline{H}$₂CH₂), 3.67 (2H, t, J=6.3 Hz, CH₂OC), 3.77 (1H, septet, J=6.3 Hz, CH), 4.49 (2H, t, J=6.3 Hz, CH₂ON), 4.65 (2H, s, OCH₂O), 8.81 (1H, s, H-8), 9.37 (1H, d, J=9.1 Hz, C$\underline{H}$O), 11.30 (1H, br.s, J=9.1 Hz, NH).

b) A mixture of 6-chloro-2-formamido-9-[3-(isopropoxymethoxy)propoxy]purine (1.86 g, 5.40 mmol), 10% palladium on charcoal (190 mg), triethylamine (3.8 ml, 27 mmol) and methanol (30 ml) was stirred under an atmosphere of hydrogen at 20° C. for 4 hr. The suspension was filtered, the catalyst washed with chloroform and the combined filtrates evaporated under reduced pressure. The residue was dissolved in dichloromethane (50 ml), washed with saturated brine-water (2:1), dried (magnesium sulphate) and evaporated. The residue was dissolved in 0.5M sodium methoxide in methanol (21.6 ml) and heated at reflux for 1 hr. The solution was taken to neutrality using AMBERLITE IR 120(H) and evaporated. The residue was purified by column chromatography on silica gel eluting with chloroform-methanol (20:1) affording the title compound (630 mg, 41%) after recrystallisation from acetone-hexane; $\nu_{max}$(KBr) 3333, 3192, 1661, 1623, 1577, 1516, 1433 cm$^{-1}$; $\delta_H$[(CD₃)₂SO] 1.09 (6H, d, J 6.05 Hz, 2×CH₃), 1.95 (2H, quintet, J 6.6 and 6.3 Hz, CH₂CH₂CH₂), 3.63 (2H, t, J=6.3 Hz, CH₂OC), 3.77 (1H, septet, J=6.0 Hz, CH), 4.39 (2H, J=6.6 Hz, CH₂ON), 4.64 (2H, s, OCH₂O), 6.69 (2H, br.s, D₂O exchangeable, NH₂), 8.31 (1H, s, H-8), 8.59 (1H, s, H-6). Found: C, 51.21; H, 6.84; N, 24.82%; C₁₂H₁₉N₅O₃ requires: C, 51.22; H, 6.82; N, 24.89%.

EXAMPLE 2

2-Amino-9-[3-(methoxymethoxy)propoxy]purine a) A mixture of 4-chloro-2,5-diformamido-6-[3-(methoxymethoxy)propoxy]pyrimidine (1.2 g, 3.80 mmol) and diethoxymethyl acetate (10 ml) was heated at 120° C. for 1 hr, then cooled and evaporated. The residue was taken up into methanol (10 ml) and concentrated aqueous ammonia (1 ml) and stirred at 20° C. for 1 hr. The solvent was then removed in vacuo. The residue was purified by column chromatography on silica gel eluting with ethyl acetate-hexane (1:1) affording 6-chloro-2-formamido-9-[3-(methoxymethoxy)-propoxy]-purine (0.45 g, 1.42 mmol) which was dissolved in methanol (30 ml), and treated with excess triethylamine (1 ml). The flask was flushed with nitrogen, palladium on carbon (10%, 40 mg) was added and the mixture was hydrogenated at S.T.P. until hydrogen uptake ceased. The reaction mixture was filtered, the filtrate evaporated in vacuo and the residue purified by crystallisation from methanol to give 2-formamido-9-[3-(methoxymethoxy)propoxy]purine as colourless crystals (0.4 g, 100%) mp. 115°-116° C. $\lambda_{max}$ (MeOH) 231 ($\epsilon$23,880), 255 (8120) and 290 nm (9430); $\nu_{max}$(KBr) 3120, 3070, 2930, 2810, 1690, 1610, 1510, 1445, 1410, and 1375 cm$^{-1}$. $\delta_H$[(CD₃)₂SO] 1.98 (2H, quintet, J=6.3 Hz, CH₂CH$\underline{H}$₂CH₂), 3.25 (3H, s, OCH₃), 3.67 (2H, t, J=6.3 Hz, CH$\underline{H}$₂OCH₂OCH₃), 4.5 (2H, t, J 6.3 Hz, CH₂ON), 4.58 (2H, s, OCH₂O), 8.73 (1H, s, 8-H), 8.98 (1H, s, 6-H), 9.42 (1H, d, J=9.6 Hz, collapses to singlet on D₂O NHCHO), 11.1 (1H, d, J=9.6 Hz, D₂O exchangeable NHC$\overline{H}$O). (Found: C, 47.11; H, 5.27; N, 24.18%; C₁₁H₁₅N₅O₄ requires: C, 46.97; H, 5.37; N, 24.90%).

b) A solution of 2-formamido-9-[3-(methoxymethoxy)propoxy]purine (0.4 g, 1.42 mmol) in methanol (15 ml) was treated with sodium methoxide solution (0.5M, 5 ml) and heated to reflux for 2 hr. The cooled reaction mixture was neutralised with AMBERLITE IR 120H resin, filtered and the solvent was removed in vacuo. The residue was dissolved in ethyl acetate (50 ml), washed with water (2×20 ml), dried (MgSO₄), filtered and the filtrate evaporated in vacuo. The residue was purified by column chromatography on silica eluting with ethyl acetate, followed by crystallisation from acetone/hexane to give the title compound as colourless crystals (0.2 g, 55%) mp 80°-1° C. $\lambda_{max}$ (MeOH) 223 ($\epsilon$26,375), 245 (5020) and 310 nm (7320); $\nu_{max}$(KBr) 3320, 3180, 3080, 2940, 2880, 1645, 1610, 1580, 1505, 1465, and 1430 cm$^{-1}$; $\delta_H$[(CD₃)₂SO] 1.95 (2H, quintet, J=6.3 Hz, CH₂CH₂CH₂), 3.25 (3H, s, OCH₃), 3.63 (2H, t, J=6.3 Hz, CH$\underline{2}$OCH₂OCH₃), 4.40 (2H, t, J=6.3 Hz, CH₂ON), 4.57 (2H, s, OCH₂O), 6.68 (2H, br.s, D₂O exchangeable NH₂), 8.3 (1H, s, 8-H), 8.59 (1H, s, 6-H). (Found: C, 47.34, H 6.08% C₁₀H₁₅N₅O₃ requires: C, 47.42; H, 59.7%).

EXAMPLE 3

9-[3-(Isopropoxymethoxy)propoxy]guanine a) Diethyl azodicarboxylate (1.24 ml, 7.87 mmol) was added to a cooled solution of 2-[(bis-t-butoxycarbonyl)amino]-9-hydroxy-6-methoxypurine (2.0 g, 5.23 mmol), 3-(isopropoxymethoxy)propanol (0.85 g, 5.75 mmol), and triphenylphosphine (2.06 g, 7.87 mmol) in THF (50 ml). The reaction mixture was stirred for 16 hours, and then evaporated under reduced pressure. The residue was purified by column chromatography on silica gel (hexane-acetone, 3:1) affording 2-[(bis-t-butoxycarbonyl)amino]-9-[3-(isopropoxymethoxy)propoxy]-6-methoxypurine (2.23 g, 83%). $\nu_{max}$ (KBr), 2975, 1788, 1761, 1597 and 1389 cm$^{-1}$; $\delta_H$[(CD₃)₂SO] 1.90 (6H, d, J=6.3 Hz, 2×CH₃), 1.40 (18H, s, 6×CH₃), 1.96 (2H, quintet, J=6.3 Hz, OCH₂C$\underline{H}$₂CH₂O), 3.64 (2H, t, J=6.3 Hz, CH₂O), 3.78 (1H, quintet, J=6.3 Hz, CHO), 4.08 (2H, s, OCH₃), 4.48 (2H, t, J=6.3 Hz, CH₂ON), 4.63 (2H, s, OCH₂O), 8.74 (1H, s, H-8). (Found: C, 54.09; H, 7.59; N, 13.65%. C₂₃H₃₇N₅O₈ requires: C, 53.99; H, 7.30; N, 13.69%).

b) A solution of 2-[(bis-t-butoxycarbonyl)amino]-9-[3-(isopropoxymethoxy)propoxy]-6-methoxypurine in 0.5M sodium methoxide in methanol (33 ml) was heated at reflux temperature for 16 hours. 2-Mercaptoethanol (1.3 ml) was then added and the reaction mixture heated for a further 48 hours. The suspension was cooled, neutralised and evaporated to dryness. The residue was purified by reverse phase chromatography eluting with water then water-methanol-concentrated aqueous ammonia (10:1:1), to afford the title compound (390 mg; 34%) after recrystallisation from water. $\nu_{max}$(KBr) 3332, 3131, 3168, 1695, 1599, 1586 and 1384 cm$^{-1}$; $\delta_H$[(CD$_3$)$_2$SO] 1.09 (6H, d, J=6.1 Hz, 2×CH$_3$), 1.91 (2H, quintet, J=6.6 Hz, 6.3 Hz, OCH$_2$CH$_2$CH$_2$O), 3.61 (2H, t, J=6.3 Hz, CH$_2$O), 3.77 (1H, septet, J=6.0 Hz, CHO), 4.32 (2H, t, J=6.6 Hz, CH$_2$ON), 4.63 (2H, s, OCH$_2$O), 6.58 (2H, br.s, NH$_2$), 7.93 (1H, s, H-8), 0.64 (1H, br.s, H-1). (Found: C, 48.58; H, 6.39; N, 23.44%. C$_{12}$H$_{19}$N$_5$O$_4$ requires C: 48.47; H, 6.45; N, 23.56%).

EXAMPLE 4

9-[3-(Ethoxymethoxy)propoxy]guanine a) A mixture of 2-[(bis-t-butoxycarbonyl)amino]-9-hydroxy-6-methoxypurine (2.85 g, 7.48 mmol), 3-(ethoxymethoxy)propan-1-ol (1.0 g, 7.46 mmol) and triphenylphosphine (2.62 g, 10 mmol) in dry tetrahydrofuran (50 ml) was cooled to 0°-5° C. and treated with a solution of diethyl azodicarboxylate (1.74 g, 10 mmol) in dry tetrahydrofuran (10 ml), the solution was then allowed to stand at room temperature overnight. The solvent was then removed in vacuo and the residue was purified by column chromatography on silica, eluting with hexane:acetone (95:5) to give 2-[(bis-t-butoxycarbonyl)amino]-9-[3-(ethoxymethoxy)propoxy]-6-methoxypurine as a yellow gum (1.7 g, 46%). $\nu_{max}$(Film) 3120, 2980, 2940, 2880, 1795, 1760, 1595, 1475, 1410, 1390, 1370, 1280 and 1255 cm$^{-1}$; $\delta_H$[(CD$_3$)$_2$SO] 1.10 (3H, t, J=6.8 Hz, CH$_3$CH$_2$), 1.4 (18H, s, CH$_3$×6), 1.96 (2H, m, J=6.3 Hz, CH$_2$CH$_2$CH$_2$), 3.47 (2H, q, J=6.8 Hz, CH$_3$CH$_2$), 3.64 (2H, t, J=6.3 Hz, CH$_2$CH$_2$ON), 4.07 (3H, s, OCH$_3$), 4.47 (2H, t, J=6.3 Hz, OCH$_2$CH$_2$), 4.6 (2H, s, OCH$_2$O), 8.74 (1H, s, 8-H). (Found: C, 52.57; H, 7.18; N, 13.92%; C$_{22}$H$_{35}$N$_5$O$_8$ requires: C, 53.10; H, 7.09; N, 14.07%) MS (70eV) m/z=498 (MH+).

b) A solution of 2-[(bis-t-butoxycarbonyl)amino]-9-[3-(ethoxymethoxy)propoxy]-6-methoxypurine (0.7 g, 1.4 mmol) in sodium methoxide (0.5M, 25 ml) was heated to reflux for 18 hr. 2-Mercaptoethanol (1 ml) was then added to the solution and heating was continued for a further 18 hr. The cooled reaction mixture was neutralised with hydrochloric acid solution (0.5M) and the solvent was removed in vacuo. The residue was purified by column chromatography on silica eluting with chloroform:methanol (90:10) followed by crystallisation from methanol to give the title compound as colourless crystals (0.1 g, 25%) mp 242°-5° C. $\lambda_{max}$(MeOH) 250 nm (14080); $\nu_{max}$(KBr) 3320, 3160, 2870, 2730, 1690, 1645, 1590, 1535, 1470, 1385 and 1320 cm$^{-1}$; $\delta_H$[(CD$_3$)$_2$SO] 1.11 (3H, t, J=7.1 Hz, CH$_2$CH$_3$), 1.92 (2H, m, J=6.5 Hz, CH$_2$CH$_2$CH$_2$), 3.5 (2H, q, J=7.1 Hz, CH$_2$CH$_3$), 3.61 (2H, t, J=6.3 Hz, CH$_2$CH$_2$ON), 4.32 (2H, t, J=6.3 Hz, OCH$_2$CH$_2$), 4.60 (2H, s, OCH$_2$O), 6.57 (2H, br.s, D$_2$O exchangeable, NH$_2$), 7.92 (1H, s, 8-H), 10.63 (1H, br.s, D$_2$O exchangeable, NH). (Found: C, 46.64; H, 5.78; N, 24.55%; C$_{11}$H$_{17}$N$_5$O$_4$ requires: C, 46.63; H, 6.05; N, 24.72%) MS (70 eV) m/z=284 (MH+).

EXAMPLE 5

2-Amino-9-[3-(ethoxymethoxy)propoxy]purine a) A solution of 2-[(bis-t-butoxycarbonyl)amino]-6-chloro-9-hydroxypurine (2.4 g, 7.4 mmol), 3-(ethoxymethoxy)propan-1-ol (1.0 g, 7.4 mmol) and triphenylphosphine (2.62 g, 10 mmol) in dry tetrahydrofuran (35 ml) was cooled to 0°-5° C. and treated with a solution of diethyl azodicarboxylate (1.75 g, 10 mmol) in dry tetrahydrofuran (10 ml). The solution was allowed to stand at room temperature overnight, the solvent was evaporated in vacuo and the residue purified by column chromatography on silica eluting with chloroform:methanol (98:2) followed by a further column eluting with hexane:acetone (90:10) to give 2-[(bis-t-butoxycarbonyl)amino]-6-chloro-9-[3-(ethoxymethoxy)propoxy]purine as a colourless gum. (1.7 g, 46%). $\nu_{max}$(Film) 3100, 2980, 2930, 2880, 1795, 1760, 1600, 1560, 1425, 1370, 1280 and 1155 cm$^{-1}$; $\delta_H$[(CD$_3$)$_2$SO] 1.11 (3H, t, J=7.1 Hz, CH$_3$CH$_2$), 1.4 (18H, s, CH$_3$×6), 2.01 (2H, m, J=6.3 Hz, CH$_2$CH$_2$CH$_2$), 3.5 (2H, q, J=7.1 Hz, CH$_3$CH$_2$), 3.64 (2H, t, J=6.3 Hz, CH$_2$CH$_2$ON), 4.55 (2H, t, J=6.3 Hz, OCH$_2$CH$_2$), 4.6 (2H, s, OCH$_2$O), 9.08 (1H, s, 8-H). (Found: C, 50.28; H, 6.55; N, 13.70%; C$_{21}$H$_{32}$N$_5$O$_7$Cl requires: C, 50.24; H, 6.42; N, 13.95%); MS (70 eV) m/z=502 (MH+).

b) To a solution of 2-[(bis-t-butoxycarbonyl)-amino]-6-chloro-9-[3-(ethoxymethoxy)propoxy]purine (1.5 g, 2.98 mmol) in methanol (25 ml) and triethylamine (1 ml) under a nitrogen atmosphere was added palladium on carbon (5%, 0.1 g) and the mixture was hydrogenated at S.T.P. until hydrogen uptake ceased. The reaction mixture was filtered and evaporated in vacuo and, the residue was purified by column chromatography on silica, eluting with ethyl acetate:hexane (50:50) to give 2-[(bis-t-butoxycarbonyl)amino]-9-[3-(ethoxymethoxy)propoxy]purine as a colourless gum. (1.2 g, 86%). $\nu_{max}$ (Film) 3100, 2980, 2930, 2880, 1790, 1735, 1600, 1575, 1480, 1455, 1390, 1370, 1280 and 1250 cm$^{-1}$; $\delta_H$[(CD$_3$)$_2$SO] 1.11 (3H, t, J=7.1 Hz, CH$_2$CH$_3$), 1.38 (18H, s, CH$_3$×6), 1.98 (2H, m, J=6.3 Hz, CH$_2$CH$_2$CH$_2$), 3.5 (2H, q, J=7.1 Hz, CH$_2$CH$_3$), 3.65 (2H, t, J=6.3 Hz, CH$_2$CH$_2$ON), 4.52 (2H, t, J=6.3 Hz, OCH$_2$CH$_2$), 4.60 (2H, s, OCH$_2$O), 8.98 (1H, s, 8-H), 9.21 (1H, s, 6-H). (Found: C, 53.88; H, 7.26; N, 15.13%; C$_{21}$H$_{33}$N$_5$O$_7$ requires: C, 53.94, H, 7.11; N, 14.98%) MS (70 eV) m/z=468 (MH+).

c) 2-[(Bis-t-butoxycarbonyl)amino]-9-[3-(ethoxymethoxy)propoxy]purine (0.5 g, 1.07 mmol) was dissolved in sodium methoxide solution (0.5M, 30 ml) and heated to reflux for 18 hr. The cooled reaction mixture was evaporated in vacuo and the residue was purified by column chromatography on silica, eluting with ethyl acetate:hexane (60:40) followed by crystallisation from acetone:hexane to give the title compound as colourless crystals (0.25 g, 89%) mp 73°-4° C. $\lambda_{max}$(MeOH) 224, 246 and 310 nm. (5610, 3750 and 20,700); $\nu_{max}$(KBr) 3370, 3330, 3200, 3080, 2930, 2880, 1645, 1615, 1570, 1505, 1475, 1425, 1320, 1280 and 1220 cm$^{-1}$; $\delta_H$[(CD$_3$)$_2$SO] 1.11 (3H, t, J=7.1 Hz, CH$_2$CH$_3$), 1.95 (2H, m, J=6.3 Hz, CH$_2$CH$_2$CH$_2$), 3.50 (2H, q, J=7.1 Hz, CH$_2$CH$_3$), 3.63 (2H, t, J=6.3 Hz, CH$_2$CH$_2$ON), 4.4 (2H, t, J=6.6 Hz, OCH$_2$CH$_2$), 4.61 (2H, s, OCH$_2$O), 6.69 (2H, br.s, D$_2$O exchangeable, NH$_2$), 8.31 (1H, s, 8-H), 8.59 (1H, s, 6-H). (Found: C, 49.48; H, 6.50; N, 26.33%; C$_{11}$H$_{17}$N$_5$O$_3$ requires: C, 49.42; H, 6.41; N, 26.20%); MS (70 eV)m/z =268 (MH+).

BIOLOGICAL EVALUATION

Procedure

Compounds were administered as single doses of 0.2 mmol/kg in 0.1 ml of 1% carboxymethyl cellulose by oral gavage to female Balb/c mice weighing 20 g. Food was withheld from the mice for 18 hours prior to the start of the experiment. Blood was collected by cardiac puncture using heparinised syringes 15, 60 and 180 mins after dosing. Equal volumes (0.2 ml) from 3 mice were pooled at each time point and 0.6 ml of ice-cold ethanol was added. Following chilling at $-20°$ C. and centrifugation, 0.5 ml of supernatant was dried under reduced pressure. The sample was then reconstituted with 0.5 ml of 0.4M $NH_4OAc$ (pH 6.0) and analysed by HPLC.

Results

| Compound of Example No. | 9-(3-Hydroxypropoxy)guanine (E1) conc. (μM) in blood at time (min) after dosing | | |
|---|---|---|---|
| | 15 | 60 | |
| 1 | 137 | 54 | Expt. 1 |
| 2 | 36 | 14 | |
| E1 | 5.2 | 2.0 | |
| 1 | 76 | 12 | Expt. 2 |
| 3 | 7.5 | 4.7 | |
| 4 | 2.1 | 4.6 | |
| 5 | 7.9 | 10 | |
| E1 | 11 | 3.3 | |

Figure 1:
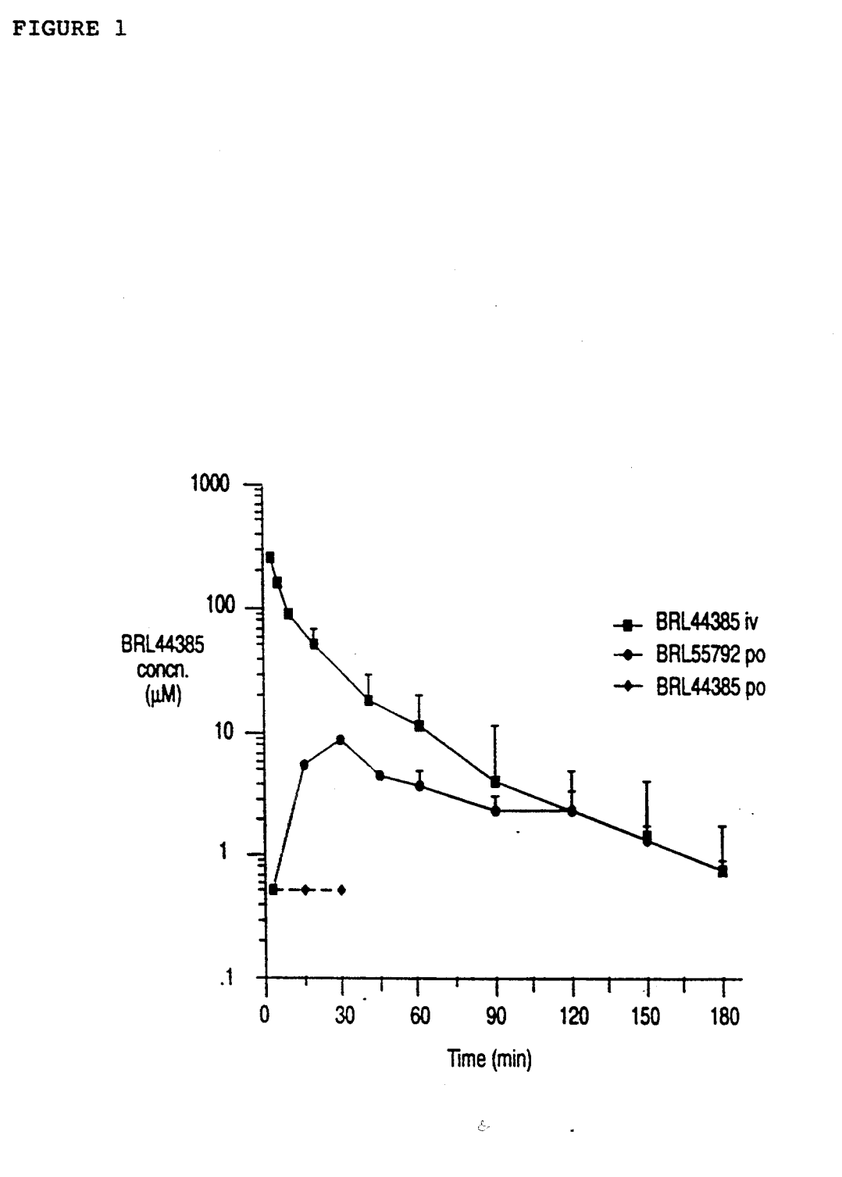

FIG. 1

Bioavailability of BRL44385 in rats following administration of oral and intravenous BRL44385 and oral BRL55792.

Compounds were administered as a single 0.2 mmol/kg dose to rats with an indwelling cannula. Sequential blood samples were collected up to 3 h after compound administration. BRL44385 concentrations were determined as described in Table 1.

Figure 2:
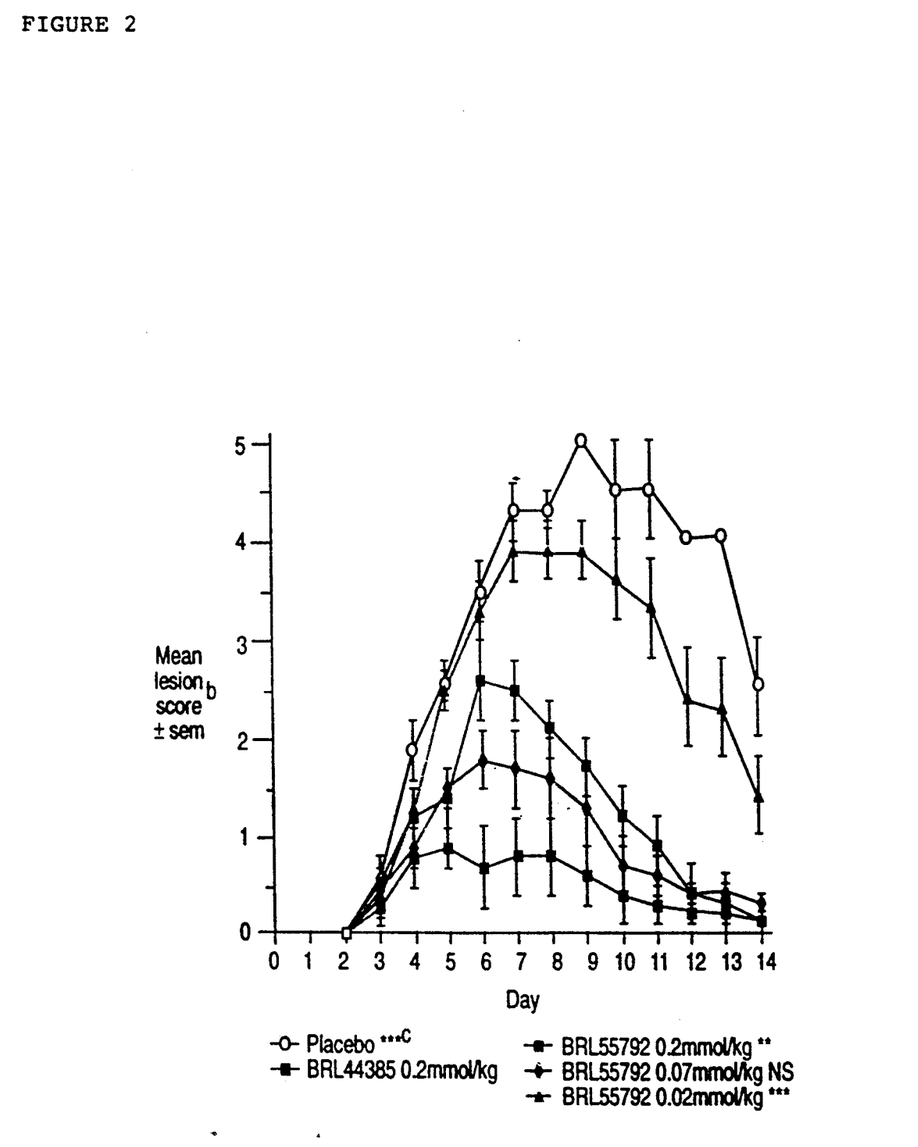

FIG. 2

Comparison of the oral efficacy of BRL44385 and BRL55792 against a cutaneous HSV-1 infection in the ear pinna of mice.

a) Groups of 10 mice were cutaneously infected in the right ear pinna with $5 \times 10^5$ PFU of HSV-1 strain SC16. Compounds were administered orally twice daily for 5 days starting 1 h after infection.

b) Lesion scoring: 0, no sign of infection; 1, erythema and/or 1-2 isolated vesicles; 2, several isolated vesicles; 3, multiple isolated vesicles; 4, coalesced vesicles; 5, ulcerative lesion.

c) Significance vs BRL44385 (0.2 mmol/kg) based on area-under-the-lesion-score/time-curves; , $p<0.01$; *, $p<0.001$; NS, not significant.

TABLE 1

Concentrations of BRL44385 and its Prodrugs Detected in the Blood of Mice after Oral Administration of 9-(Alkoxymethoxypropoxy)purines[a]

| Compound dosed | | | Concn (μM) in blood at time (min) after dosing[b] | | | |
|---|---|---|---|---|---|---|
| | | | total 9-alkoxypurines | | BRL44385 | |
| BRL No | X | R | 15 | 60 | 15 | 60 |
| 44385 | OH | H | 8.9 | 4.0 | 8.9 | 4.0 |
| 46720 | H | H | 54 | 5.0 | 45 | 4.0 |
| 55791 | H | $MeOCH_2$ | 149 | 48 | 36 | 14 |
| 57040 | OH | $EtOCH_2$ | 2.1 | 8.6 | 2.1 | 4.6 |
| 57041 | H | $EtOCH_2$ | 17 | 14 | 8 | 10 |
| 57037 | OH | $i$-$PrOCH_2$ | 25 | 6.7 | 7.5 | 4.7 |
| 55792 | H | $i$-$PrOCH_2$ | 117 | 24 | 87 | 24 |

[a] Compounds were administered as single doses of 0.2 mmol/kg in 0.1 ml of 1% (carboxymethyl)cellulose by oral gavage to female Balb/c mice weighing approximately 20 g. Food was withheld for 18 h prior to the start of the experiment. Blood was collected by cardiac puncture using heparinised syringes 15, 60 and 180 min after dosing. Equal volumes (0.2 ml) from three mice were pooled at each time point and 0.6 ml of 16% trichloroacetic acid was added. After centrifugation, 0.5 ml of supernatant was added to 0.1 ml of saturated aqueous $NaHCO_3$ followed by the addition of 0.6 ml of 0.4M $NH_4OAc$ (pH 6.0) and the mixture analysed by HPLC.
[b] 9-Alkoxypurine concentrations $<2$ μM were detected in the blood 180 min after dosing.

TABLE 2

Further evaluation of BRL55792 as a potential oral prodrug of BRL44385 in rats and squirrel monkeys

| Species | Compound administered[a] | Mean Area-under-the-curve[b] (μM · h) ± SEM for BRL | | | | | Relative oral bioavailability of BRL44385[c] |
|---|---|---|---|---|---|---|---|
| | | 55792 | 46720 | 57037 | 44385 | Total | |
| Rat | BRL44385 | — | — | — | ≈0.1 | ≈0.1 | 1 |
| | BRL55792 | 2.0 ± 0.8 | 0 | 7.6 ± 1.1 | 9.9 ± 0.7 | 20 ± 2.4 | 100 |
| Squirrel monkey | BRL44385 | — | — | — | 13 ± 2.4 | 13 ± 2.4 | 1 |
| | BRL55792 | 13 ± 5.7 | 2.1 ± 2.1 | 21 ± 0.7 | 43 ± 12 | 78 ± 11 | 3.3 |

[a] Compounds were administered as a single oral dose at either 0.2 mmol/kg (equivalent to 44.5 mg/kg free BRL44385) to rats with an indwelling aortic cannula or 0.11 mmol/kg (equivalent to 25 mg/kg free BRL44385) to squirrel monkeys. Sequential blood samples were collected up to 8 h after compound administration. Following treatment as described in table 1, the samples were assayed for BRL55792, BRL44385 and intermediate matabolites.
[b] Mean area-under-the-curve values were calculated from blood concentration-time profiles from 3 animals by the trapezoidal rule (0-6 h for rats and 0-8 h for squirrel monkeys).
[c] AUC of BRL44385 from prodrug/AUC of BRL44385 from oral BRL44385

We claim:

1. A compound of formula (I) or a pharmaceutically acceptable salt thereof:

(I)

wherein
$R_1$ is hydrogen or hydroxy; and
$R_2$ is $C_{1-6}$ alkyl.

2. A compound according to claim 1 wherein $R_1$ is hydrogen.

3. A compound according to claim 1 wherein $R_2$ is iso-propyl.

4. A compound selected from the group consisting of:
2-amino-9-[3-(isopropoxymethoxy)propoxy]purine,
2-amino-9-[3-(methoxymethoxy)propoxy]purine,
9-[3-(isopropoxymethoxy)propoxy]guanine,
9-[3-(ethoxymethoxy)propoxy]guanine and
2-amino-9-[3-(ethoxymethoxy)propoxy]purine.

5. 2-Amino-9-[3-isopropoxymethoxy)propoxy]purine.

6. A pharmaceutical composition comprising a compound according to claim 1, and a pharmaceutically acceptable carrier.

7. A method of treatment of herpesvirus infections in mammals, which comprises the administration to the mammal in need of such treatment, an effective amount of a compound according to claim 1.

* * * * *